US010111717B2

United States Patent
Lui et al.

(10) Patent No.: US 10,111,717 B2
(45) Date of Patent: Oct. 30, 2018

(54) SYSTEM AND METHODS FOR IMPROVING PATENT REGISTRATION

(71) Applicants: SYNAPTIVE MEDICAL (BARBADOS) INC., Bridgetown (BB); Dorothy Lui, Toronto (CA); Gal Sela, Toronto (CA); Aisha Sial, Toronto (CA); Sepide Movaghati, Toronto (CA); Kirusha Srimohanarajah, Toronto (CA); Sean Chen, Toronto (CA); Simon Alexander, Toronto (CA); Neil Witcomb, Toronto (CA)

(72) Inventors: Dorothy Lui, Toronto (CA); Gal Sela, Toronto (CA); Aisha Sial, Toronto (CA); Sepide Movaghati, Toronto (CA); Kirusha Srimohanarajah, Toronto (CA); Sean Jy-Shyang Chen, Toronto (CA); Simon Kenley Alexander, Toronto (CA); Neil Jeffrey Witcomb, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 0 days.

(21) Appl. No.: 15/553,426

(22) PCT Filed: May 2, 2016

(86) PCT No.: PCT/CA2016/050506
§ 371 (c)(1),
(2) Date: Aug. 24, 2017

(87) PCT Pub. No.: WO2017/190210
PCT Pub. Date: Nov. 9, 2017

(65) Prior Publication Data
US 2018/0168735 A1 Jun. 21, 2018

(51) Int. Cl.
*G06K 9/00* (2006.01)
*A61B 34/20* (2016.01)
(Continued)

(52) U.S. Cl.
CPC .............. *A61B 34/20* (2016.02); *A61B 34/10* (2016.02); *A61B 5/055* (2013.01); *G06T 7/30* (2017.01)

(58) Field of Classification Search
None
See application file for complete search history.

(56) References Cited

U.S. PATENT DOCUMENTS 7,398,116 B2 *  7/2008  Edwards .............. A61B 5/7289
                                                  600/424
7,751,868 B2 *  7/2010  Glossop .................. A61B 5/06
                                                  600/407

(Continued)

FOREIGN PATENT DOCUMENTS

WO        2012/169990 A2    12/2012

OTHER PUBLICATIONS

Clements, L.W. et al., "Robust surface registration using salient anatomical features for image-guided liver surgery: Algorithm and validation", Medical Physics vol. 35, No. 6, Jun. 2008, pp. 2528-2540.

(Continued)

*Primary Examiner* — Hadi Akhavannik
(74) *Attorney, Agent, or Firm* — Rowand LLP

(57) ABSTRACT

The application as disclosed herein describes systems and methods for performing patient registration using a surgical navigation system. This application attempts to provide for improvements upon existing systems through the addition of refinement steps used to increase the accuracy of registration and streamline said process. In some cases the improve- (Continued)

ments generally involve the manipulation of spatial data in an iterative manner.

20 Claims, 16 Drawing Sheets

(51) Int. Cl.
*A61B 34/10* (2016.01)
*A61B 5/055* (2006.01)
*G06T 7/30* (2017.01)

(56) References Cited

U.S. PATENT DOCUMENTS

| 9,241,657 | B2* | 1/2016 | Vollmer | A61B 5/0062 |
| 2007/0060799 | A1* | 3/2007 | Lyon | A61B 34/20 |
| | | | | 600/300 |
| 2014/0193053 | A1* | 7/2014 | Kadoury | G06T 11/008 |
| | | | | 382/131 |
| 2016/0015471 | A1* | 1/2016 | Piron | A61B 1/00059 |
| | | | | 600/424 |

OTHER PUBLICATIONS

International Search Report from PCT/CA2016/050506 dated Jan. 26, 2017.
Written Opinion from PCT/CA2016/050506 dated Jan. 26, 2017.
International Preliminary Report of Patentability from PCT/CA2016/050506 dated Aug. 8, 2017.

* cited by examiner

SYSTEM AND METHODS FOR IMPROVING PATENT REGISTRATION

TECHNICAL FIELD

The present disclosure is generally related to neurosurgical or medical procedures, and more specifically to methods for improving the surface trace patient registration process using a medical navigation system.

BACKGROUND

In the field of medicine, imaging and image guidance are a significant component of clinical care. From diagnosis and monitoring of disease, to planning of the surgical approach, to guidance during procedures and follow-up after the procedure is complete, imaging and image guidance provides effective and multifaceted treatment approaches, for a variety of procedures, including surgery and radiation therapy. Targeted stem cell delivery, adaptive chemotherapy regimes, and radiation therapy are only a few examples of procedures utilizing imaging guidance in the medical field.

Advanced imaging modalities such as Magnetic Resonance Imaging ("MRI") have led to improved rates and accuracy of detection, diagnosis and staging in several fields of medicine including neurology, where imaging of diseases such as brain cancer, stroke, Intra-Cerebral Hemorrhage ("ICH"), and neurodegenerative diseases, such as Parkinson's and Alzheimer's, are performed. As an imaging modality, MRI enables three-dimensional visualization of tissue with high contrast in soft tissue without the use of ionizing radiation. This modality is often used in conjunction with other modalities such as Ultrasound ("US"), Positron Emission Tomography ("PET") and Computed X-ray Tomography ("CT"), by examining the same tissue using the different physical principals available with each modality. CT is often used to visualize boney structures and blood vessels when used in conjunction with an intra-venous agent such as an iodinated contrast agent. MRI may also be performed using a similar contrast agent, such as an intra-venous gadolinium based contrast agent which has pharmaco-kinetic properties that enable visualization of tumors and break-down of the blood brain barrier. These multi-modality solutions can provide varying degrees of contrast between different tissue types, tissue function, and disease states. Imaging modalities can be used in isolation, or in combination to better differentiate and diagnose disease.

In neurosurgery, for example, brain tumors are typically excised through an open craniotomy approach guided by imaging. The data collected in these solutions typically consists of CT scans with an associated contrast agent, such as iodinated contrast agent, as well as MRI scans with an associated contrast agent, such as gadolinium contrast agent. Also, optical imaging is often used in the form of a microscope to differentiate the boundaries of the tumor from healthy tissue, known as the peripheral zone. Tracking of instruments relative to the patient and the associated imaging data is also often achieved by way of external hardware systems such as mechanical arms, or radiofrequency or optical tracking devices. As a set, these devices are commonly referred to as surgical navigation systems.

During a medical procedure, navigation systems require a registration process to transform between the physical position of the patient in the operating room and the volumetric image set (e.g., MRI/CT) being used as a reference to assist in accessing the target area in the patient. Conventionally, this registration is done relative to the position of a patient reference, which is visible by the tracking system and stays fixed in position and orientation relative to the patient throughout the procedure.

This registration is typically accomplished through a touch-point registration method which involves constructing a correspondence of identifiable points (e.g., either fiducial or anatomic points) between the patient in the operating room and the volumetric image set of the patient. Such an approach to registration has a number of disadvantages, such as those that increase effort on the parts of the surgical team including requiring fiducials to be placed before patient scans, requiring points to be identified one at a time, requiring points to be reacquired. Additionally disadvantages of this method also affect the accuracy of the guidance system, such as providing for a limited number of points, touch point collection is subject to user variability, and the physical stylus used for collecting the points can deform or deflect patient skin position, in addition the patient is required to be imaged directly before the procedure and the fiducials may move/fall off.

Another approach to performing a registration is the surface trace registration method which involves acquiring a contour of the patient, by drawing a line over the surface of the patient, usually acquiring a series of points, using either a tracked stylus pointer or a laser pointer and fitting that contour to the corresponding extracted surface from an image of the patient.

SUMMARY

The following application generally discloses a computer implemented method for performing a patient registration using a processor of a surgical navigation system in a medical procedure, comprising the steps of initializing a surface trace acquisition, recording one or more surface traces, terminating the surface trace acquisition, receiving a patient image of a patient anatomy, extracting a surface from the patient image, and computing a registration transform for patient registration between the one or more surface traces and the patient image extracted surface. This method may also comprise computing the registration transform by minimizing a set of Euclidean distances. In some embodiments the step of computing a registration transform may comprise iteratively inputting registration transforms into a cost minimization function. In other embodiments the set of Euclidean distances used to compute the patient registration transform may include at least the distances between the surface traces and the extracted surface. In addition the method may comprise the steps of: initializing a fiducial position acquisition, recording the positions of fiducials on the patient, and receiving the location of fiducials points in the patient image. In other instances the set of Euclidean distances may include at least the distances between the surface traces and the extracted surface and the distances between the fiducials and the fiducial points. In yet further embodiments the method may include the steps of: monitoring the position of a pointer tool, analyzing the position to determine if the pointer tool is motionless, and upon determining that the pointer tool is motionless for a predetermined amount of time prompting the surgical navigation system to initialize or terminate the surface trace. Furthermore the method may also comprise the steps of: receiving input from a user ranking the one or more surface traces, computing a weighting for the surface traces based on the ranking, applying the weighting to the surface traces, and computing the registration transform that minimizes a set of Euclidean distances between the one or more surface traces and the surface. In yet further embodiments the methods may further comprise: receiving input from a user of one or more regions of one or more surface traces to be culled, discarding the one or more regions from the one or more surface traces, and computing a registration transform that minimizes a set of Euclidean distances between the one or more surface traces and the surface after the regions have been discarded. In some instances the method may also comprise the steps of: segmenting the patient image into regions, determining the spatial distribution of surface traces amongst the regions, determining whether the spatial distribution in each region minimize deviance below a threshold, and upon determining the spatial distribution in a region is above the threshold informing the user of the regions. It should be noted that the step of segmenting the patient image into regions, may further entail doing so such that each region contains an anatomical landmark such as the naison, the temples, the ears, the tip of the nose, the bridge of the nose, the shelves over the eyes, and etc. In some alternate instances the method may also comprise: initializing one or more landmark acquisitions, recording the positions of one or more landmarks on a patient, receiving the position of one or more landmark points in the patient image, and computing an initial registration transform that minimizes a set of Euclidean distances between the one or more landmarks and the one or more landmark points. The method as disclosed herein may also comprise using the initial registration transform to visualize an initial alignment of the patient's position with the patient image in an image space as well as visualizing the surface traces in the image space and this resultantly may assist the user in acquiring the surface traces.

Also generally disclosed in this application is a surgical navigation system used for navigated surgical procedures generally comprising: a tracked pointer tool for identifying positions on the patient, a tracking system for tracking the pointer tool, and a processor programmed with instruction to: initialize a surface trace acquisition, continuously record the positions of the pointer tool during the surface; trace acquisition, combine the positions recorded during the surface trace acquisition into a surface trace, terminate the surface trace acquisition, receive a patient image of the patient, extract a surface from the patient image, and compute a registration transform between the one or more surface traces and the surface for patient registration. It should be noted that this system may also compute a registration transform wherein this computation includes minimizing a set of Euclidean distances. In some instances the computation of a registration transform may further comprise iteratively inputting registration transforms into a cost minimization function. In yet other instances the set of Euclidean distances may include at least the distances between the surface traces and the surface. In some embodiments the processor may be programmed with further instructions comprising: initialize a fiducial position acquisition, record the position of the pointer tool during the fiducial position acquisition, and receive the location of fiducials points in the patient image. In alternate embodiments the set of Euclidean distances may include at least the distances between the surface traces and the surface and the distances between the fiducial positions and the fiducial points. In still yet alternate embodiments the processor may be programmed with further instructions comprising: monitor the position of the pointer tool with the tracking system by recording the pointer tool positions, analyze the pointer tool positions to determine if the pointer tool is motionless, and upon determining that the pointer tool is motionless for a predetermined amount of time prompting the processor to initialize the surface trace acquisition. Furthermore the processor may be programmed with further instructions comprising: receiving input from a user ranking the one or more surface traces, computing a weighting for the surface traces based on the ranking, applying the weighting to the surface traces, and computing a registration transform that minimizes a set of Euclidean distances between the one or more surface traces and the surface. Again the processor may in some instances be programmed with further instructions comprising: receiving input from a user of one or more regions of one or more surface traces to be culled, discarding the one or more regions from the one or more surface traces, and computing a registration transform that minimizes a set of Euclidean distances between the one or more surface traces and the surface after the regions have been discarded. The system as described herein my in some instances also comprise a display having a GUI for receiving input from a user, while the processor may be programmed with further instructions to: initializing one or more landmark acquisitions, recording the positions of one or more landmarks on a patient, receiving the position of one or more landmark points in the patient image; and computing an initial registration transform that minimizes a set of Euclidean distances between the one or more landmarks and the one or more landmark points. In yet further embodiments the processor may be programmed with further instructions comprising: using the initial registration transform to visualize, on the display, an initial alignment of the patient's position with the patient image in an image space and to visualize the surface traces on the display.

BRIEF DESCRIPTION OF THE DRAWINGS

Embodiments will now be described, by way of example only, with reference to the drawings, in which.

DETAILED DESCRIPTION

Figure 1:
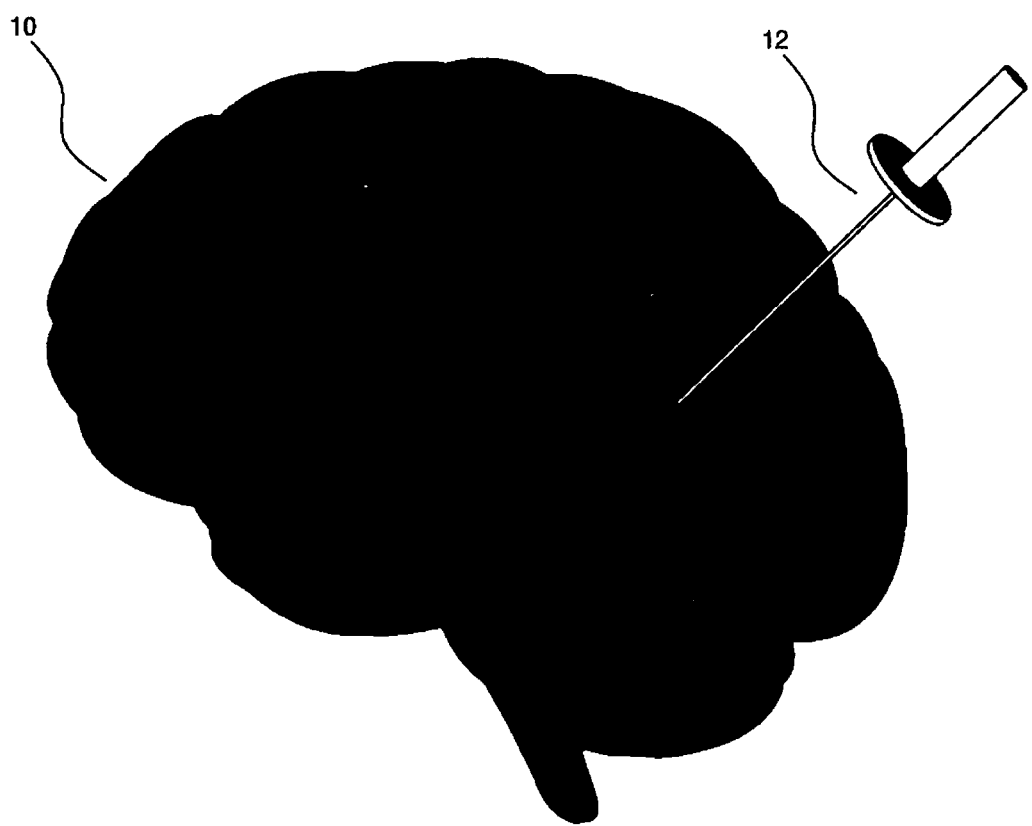
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

The present disclosure is generally related to medical procedures, neurosurgery, and patient registration to be specific.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments would then be inserted down the access port 12.

Optical tracking systems, which may be used in the medical procedure, track the position of a part of the instrument that is within line-of-site of the optical tracking camera. In some embodiments these optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked.

Figure 2:
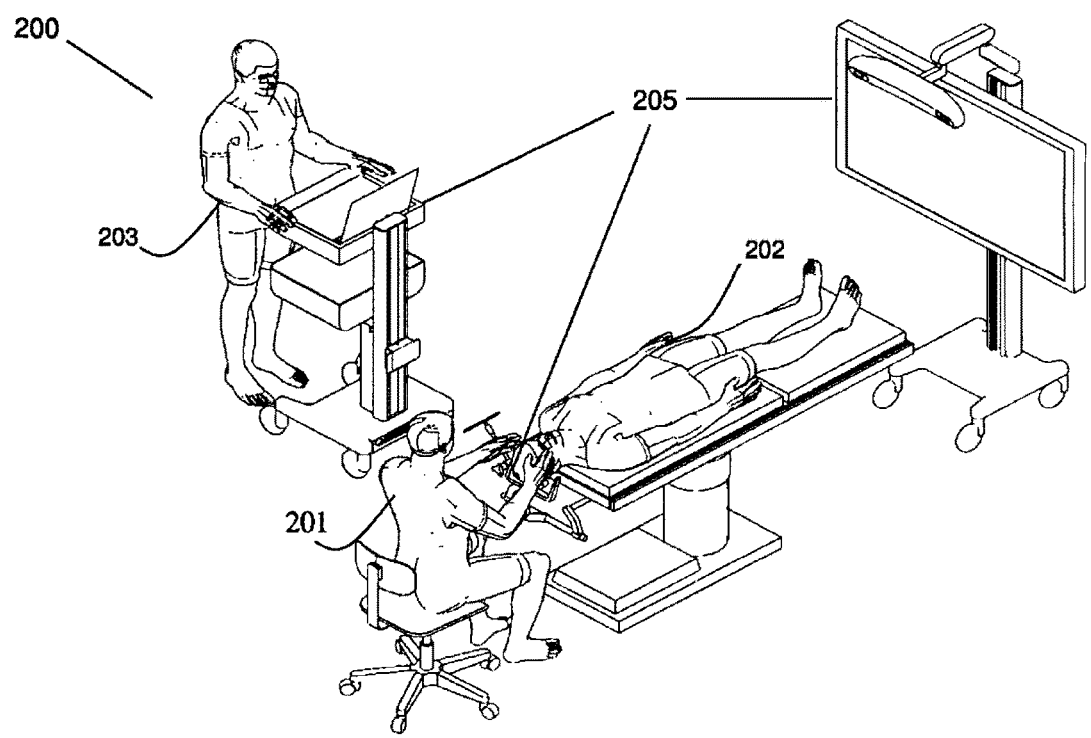
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the. 201 during his procedure. An operator 203 is also present to operate, control and provide assistance for the medical navigation system 205.

Figure 3:
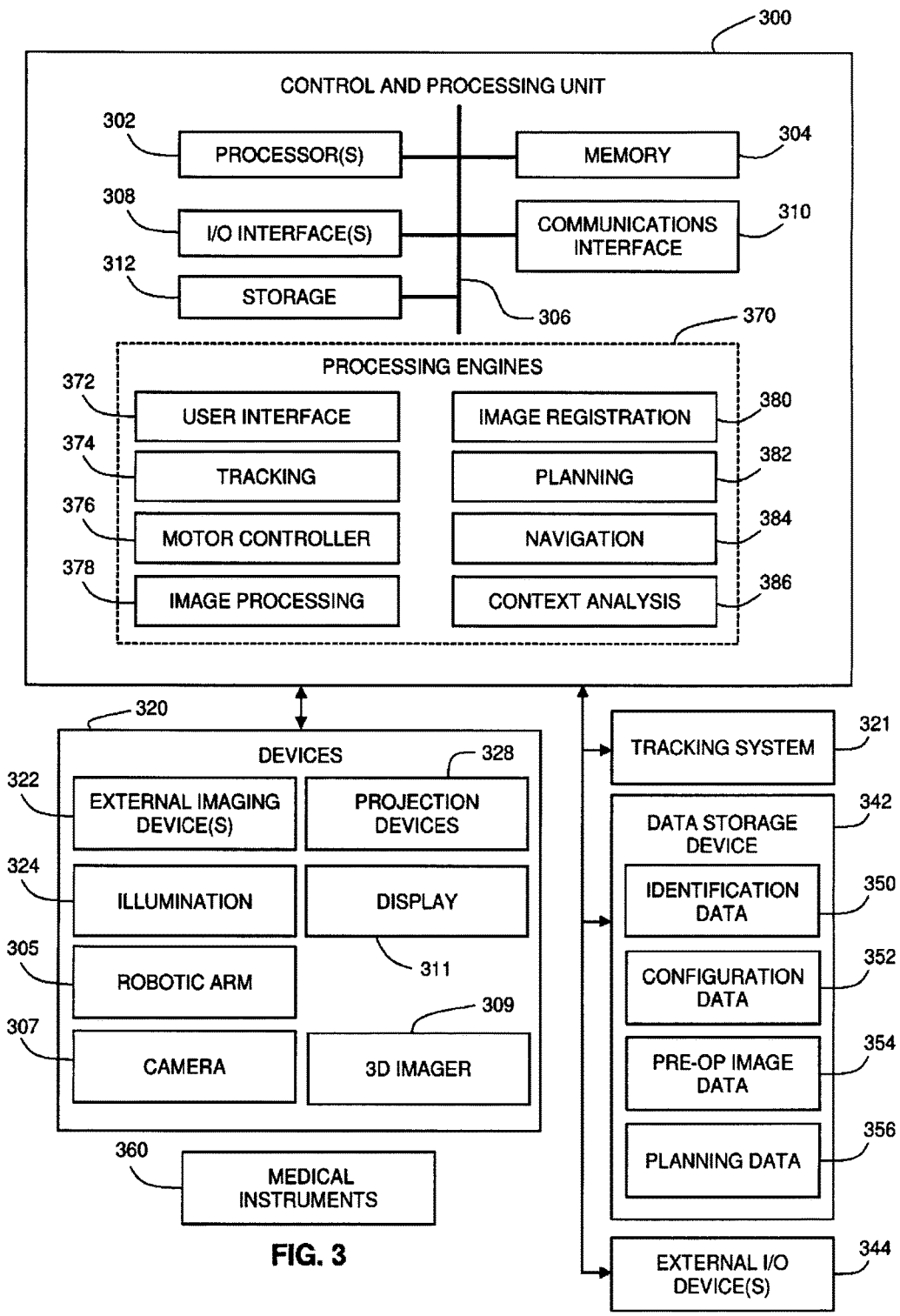
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, a 3D imager 309, and one or more displays 311. It should be noted that the 3D imager may include devices such as a preoperative or intraopertive CT, MRI, Ultrasound, OCT, or Structured light imaging probes and the like.

Exemplary aspects of the disclosure may be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using optical tracking instead of infrared cameras.

Figure 4A:
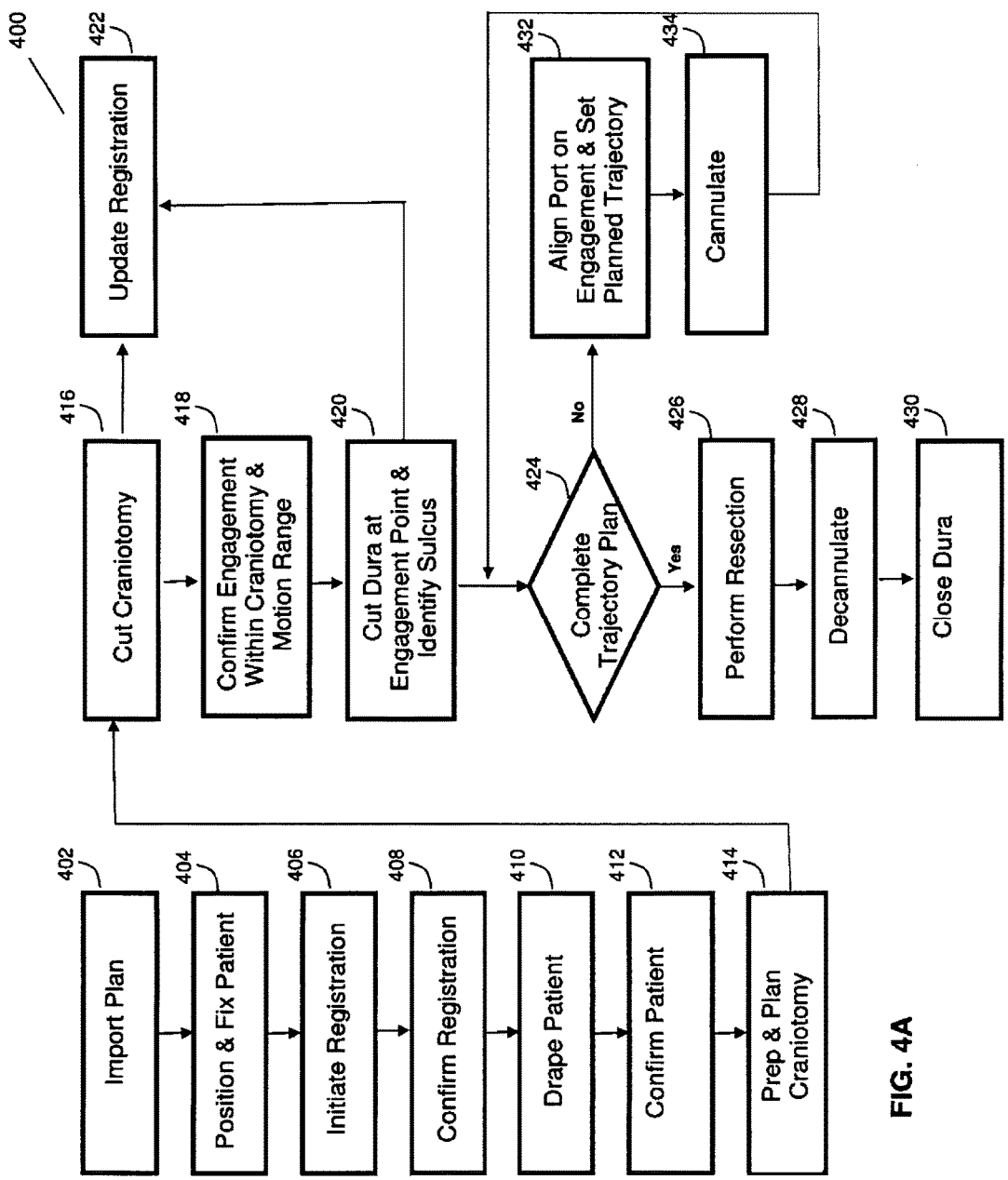
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 205 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by a computer or controller forming part of the equipment tower.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" may beused for medical imaging in which images from different imaging modalities are co-registered. In some instances registration may also be used in order to be able to compare, map, or integrate the data obtained from these different modalities with a position of a patient in physical space.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT to patient in physical space.

Figure 4B:
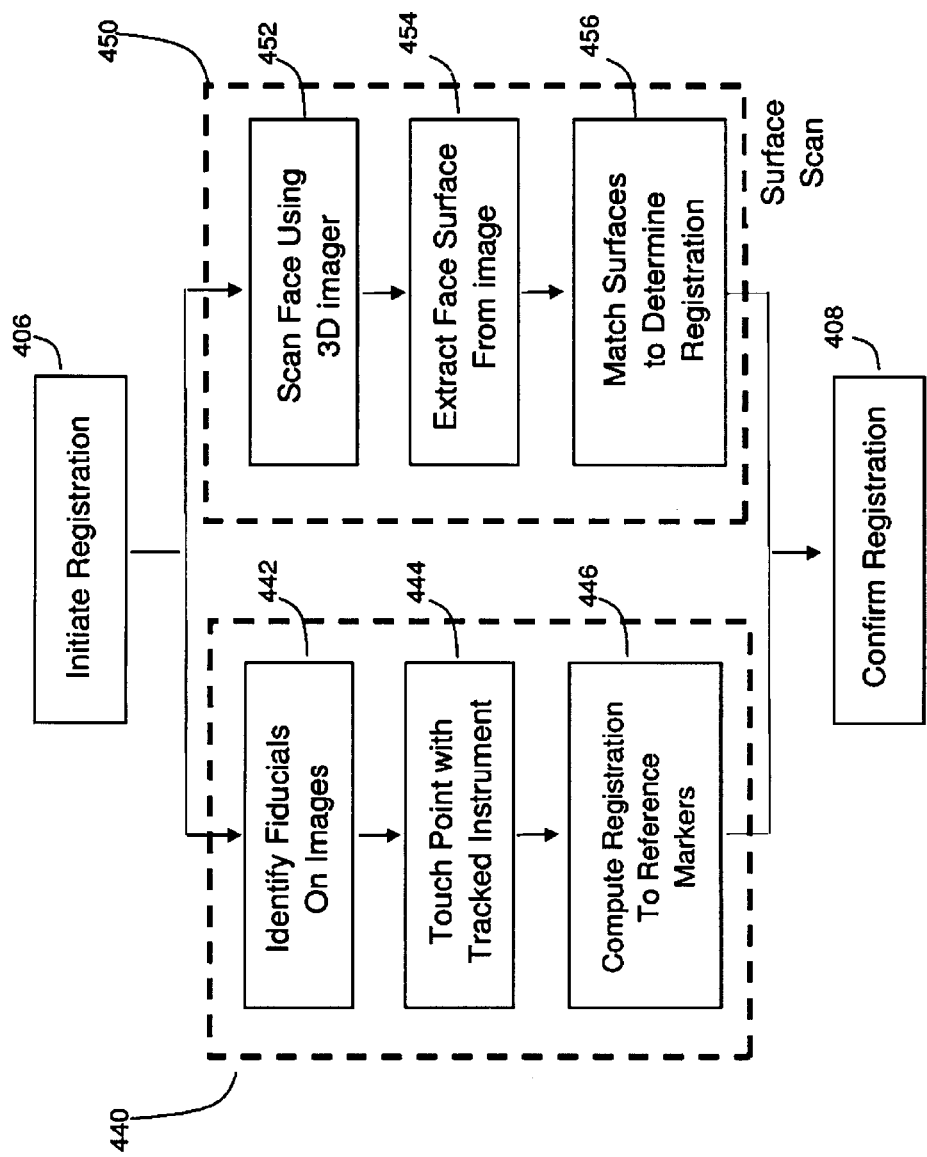
FIG. 4B is a flow chart illustrating a method of registering a patient for a surgical procedure as outlined in FIG. 4A.

Referring now to FIG. 4B, a flow chart is shown illustrating two methods which may occur as per registration block 406, outlined in FIG. 4A, in greater detail. If the use of fiducial touch points (440) is contemplated, the method involves first identifying fiducials on images (block 442), then touching the touch points with a tracked instrument (block 444). Next, the navigation system computes the patient registration to reference markers (block 446).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, generally the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

Figure 5:
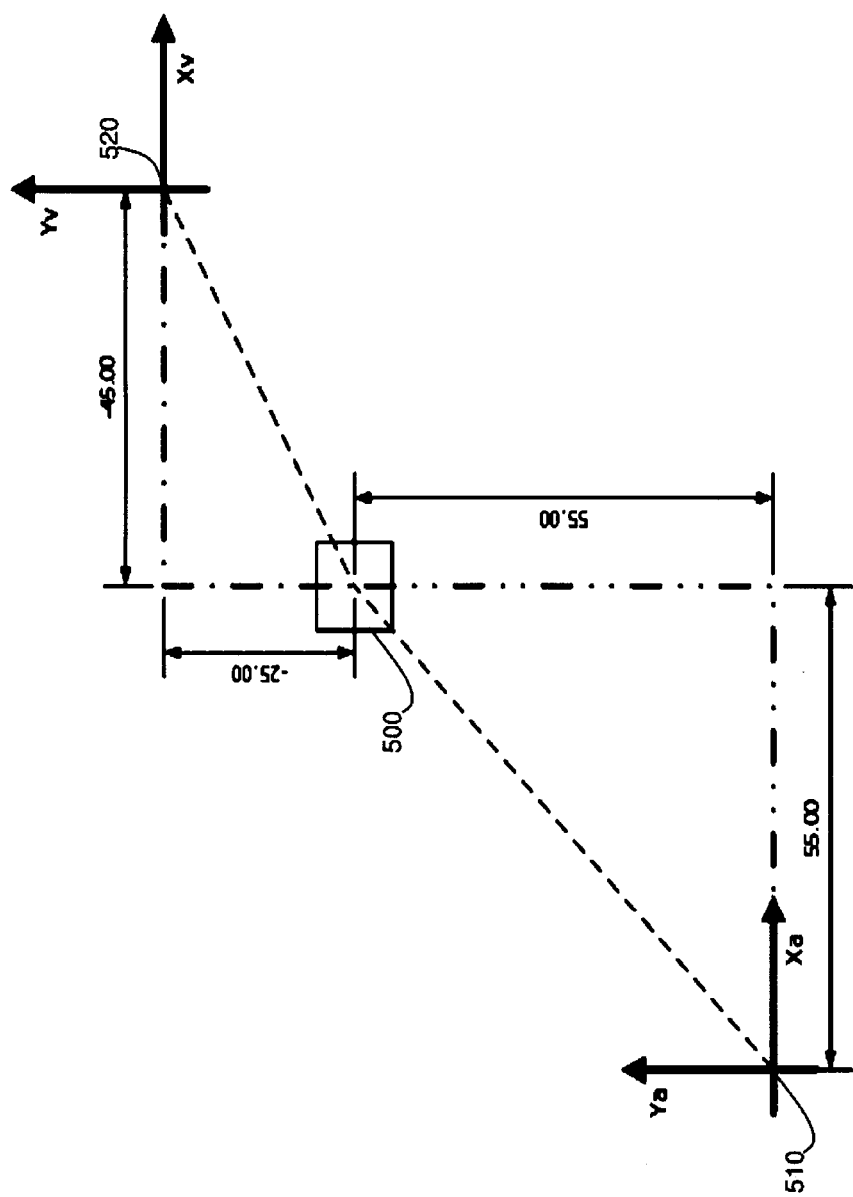
FIG. 5 illustrates an explanatory diagram regarding the coupling of two coordinate spaces.

Referring now to FIG. 5, a registration process, similar to that which may be used in block 456 of FIG. 4B, is shown for computing a transform that may be used to import coordinates from the physical coordinate space of the operating room to the image space of the MRI image. Resultantly any tool positions in the physical coordinate space may be registered to the image space via the application of this transform.

In order to derive this transform for importing objects from a physical coordinate space to an image space, the two spaces must be coupled with a "common reference", having a defined position that can be located in both the physical and image coordinate spaces. The process of patient registration for surgical navigation uses identifiable points located on a patient anatomy visible both on the patient and on the patients scan as the common reference point(s). An example of a common reference is shown in FIG. 5 as 500 along with the physical and image coordinate space origins, 510 and 520 respectively. It is apparent from the figure that the common references position is known in both spaces. Using these positions a transform may be derived that facilitates the importation of the position of any point in the physical coordinate space into the image space. One way to determine the transform is by equating the locations of the common reference in both spaces and solving for an unknown translation variable for each degree of freedom defined in the two coordinate spaces. These translation variables may then be used to convert a set of coordinates from one space to the other. An exemplary transform may be derived as per the diagram shown in FIG. 5. In the figure the position of the common reference 500 is known relative to the physical coordinate space origin 510 and the image space origin 520. The common references position can be extracted from the diagram as follows:

$$(Xcra, Ycra) = (55, 55)$$

and $$(Xcrv, Ycrv) = (-45, -25)$$

Where the subscript "cra" denotes the common reference position relative to the physical coordinate space origin and the subscript "crv" denotes the common reference position relative to the image space origin. Utilizing a generic translation equation describing any points ((Ya, Xa) and (Yv, Xv)), where the subscript "a" denotes the coordinates of a point relative to the physical coordinate space origin 510, and the subscript "v" denotes the coordinates of a point relative to the image space origin 520, we can equate the individual coordinate elements from each space to solve for translation variables ((YT, XT)), where the subscript "T" denotes the translation variable as shown below.

$Yv=Ya+YT$ $Xv=Xa+XT$

Now substituting the derived values of the points from FIG. 5 we can solve for the translation variable.

$-45=55+YT$ $100YT$

And $25=55+XT$ $80=XT$

Utilizing these translation variables, any position ((i.e. (Ya, Xa)) defined relative to the common reference in the physical coordinate space may be transformed into an equivalent position defined relative to the common reference in the image space through the two generic transformation equations provided below. It should be noted that these equations may be rearranged to transform any coordinates of a position from the image space into equivalent coordinates of a position in the physical coordinate space as well.

$Xa=Xv+100$ and $Ya=Yv+80$

The calculated transform thus enables the position of any object to be transformed from the physical coordinate space to the image space. Thus the two spaces become coupled with the transform enabling the registration of objects from the physical space to the image space. It should be noted that in practice the common reference is usually a set of points (as opposed to a single point) from the patients anatomy that may be located both on the anatomy of the patient in the physical coordinate space of the operating room and in the image of the patient. Using a set of points may be more advantages as it further restricts degrees of freedom. More specifically in a spatial coordinate system such as the physical coordinate space of the operating room an object may have six degrees of freedom, three spatial degrees of freedom most commonly referred to as (x, y, z) and three rotational degrees most commonly referred to as (pitch, yaw, roll). Accordingly one manner to duplicate these values upon transformation from the physical coordinate space to the image space is to transform three or more points from the object.

To further elaborate on the process of registration two practical implementations will be described in further detail as follows. A flow chart describing the two practical methods of performing a patient registration are provided in FIG. 6. The first method 621 is the touch-point registration method and the second method 601 is the more recently established surface trace method. FIG. 7 shows an illustrative diagram of each step in performing a registration using the touch-point method 621. These methods may be employed through the use of the navigation system and any steps may be programmed into the processor and stored in memory and called upon when needed.

The first step in this method 620 is to initiate the touch-point acquisition process. During this step a user may prompt the navigation system processor such as processor 302 in FIG. 3 to initiate a touch-point acquisition process. To clarify a touchpoint acquisition may refer to the priming of the system to acquire a pointer position upon determining it to be at the position of a fiducial point. In an alternate embodiment the system itself may initiate a touch-point registration process without the input of the user, such as upon the system advancing to the touch-point registration mode, or upon detection of trackable medical instruments such as by tracking system 321.

Once the touch-point registration process is initiated 620 the following step is to acquire one or more fiducial positions 625 in the physical coordinate space of the operating room. FIG. 7 depicts an illustration of this step 625. As is shown in the figure a user 704 is identifying fiducials 708 on a patient 707 using a tracked pointer tool 702. The tracking camera 750, connected to the surgical navigation system (not shown), collects the positions of the fiducial points 708 via the tracked pointer tool 702 and passes them to the navigation system processor which either stores the points in the image space containing the patient image, such as the points 708 in the image space 725, or alternatively in memory, or the like. In some cases the tracking system is constantly tracking the pointer tool's position. Thus in order to record the position of the pointer tool at the correct time (i.e. when it is placed on a fiducial), the system may be prompted by the user. This prompt may be facilitated through the use of a switch type device such as a foot pedal or mouse that is connected to the surgical navigation system and are read by the processor for activation. In addition an alternate way of prompting the navigation system to record the position of the pointer tool when placed on the fiducial may be through the use of a gesture. One gesture that may be used to capture the position of the pointer tool at the correct time may be statically holding the pointer tool in the same position for a predetermined amount of time. One benefit of using this gesture based switch over the manual ones is that it requires no additional hardware and may be implemented using the navigation system with the hardware as is.

Once the fiducial points are acquired 625 the following step is to extract the scanned fiducial points from the patient image 630. FIG. 7 depicts an illustration of this step. As is shown in the figure the scanned fiducials 710 are segregated from the rest of the patient image 706 in the image space 730. In some cases the segregation of the fiducials from the image of the patient may be completed manually by a user, where the user indicates the fiducial positions on the patient image to the surgical navigation system through a graphical user interface, such as 372 in FIG. 3. While in other cases the surgical navigation system may be programmed with instructions to segregate the positions of the scanned fiducials from the patient image automatically. Thus step 630 may be performed by either a user or a surgical navigation system.

Figure 7:
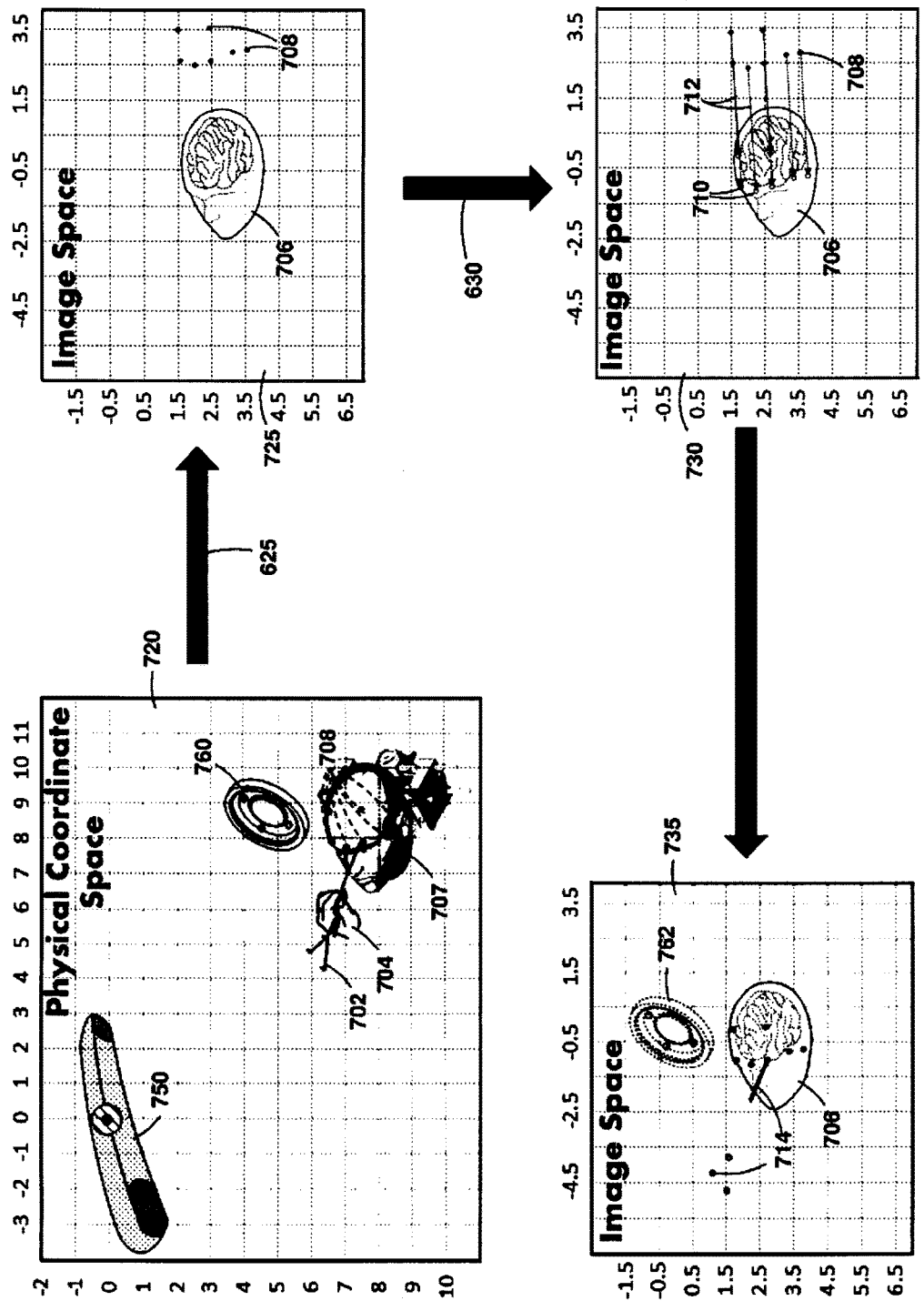
FIG. 7 is a diagram depicting one of the methods in FIG. 6.
Figure 8:
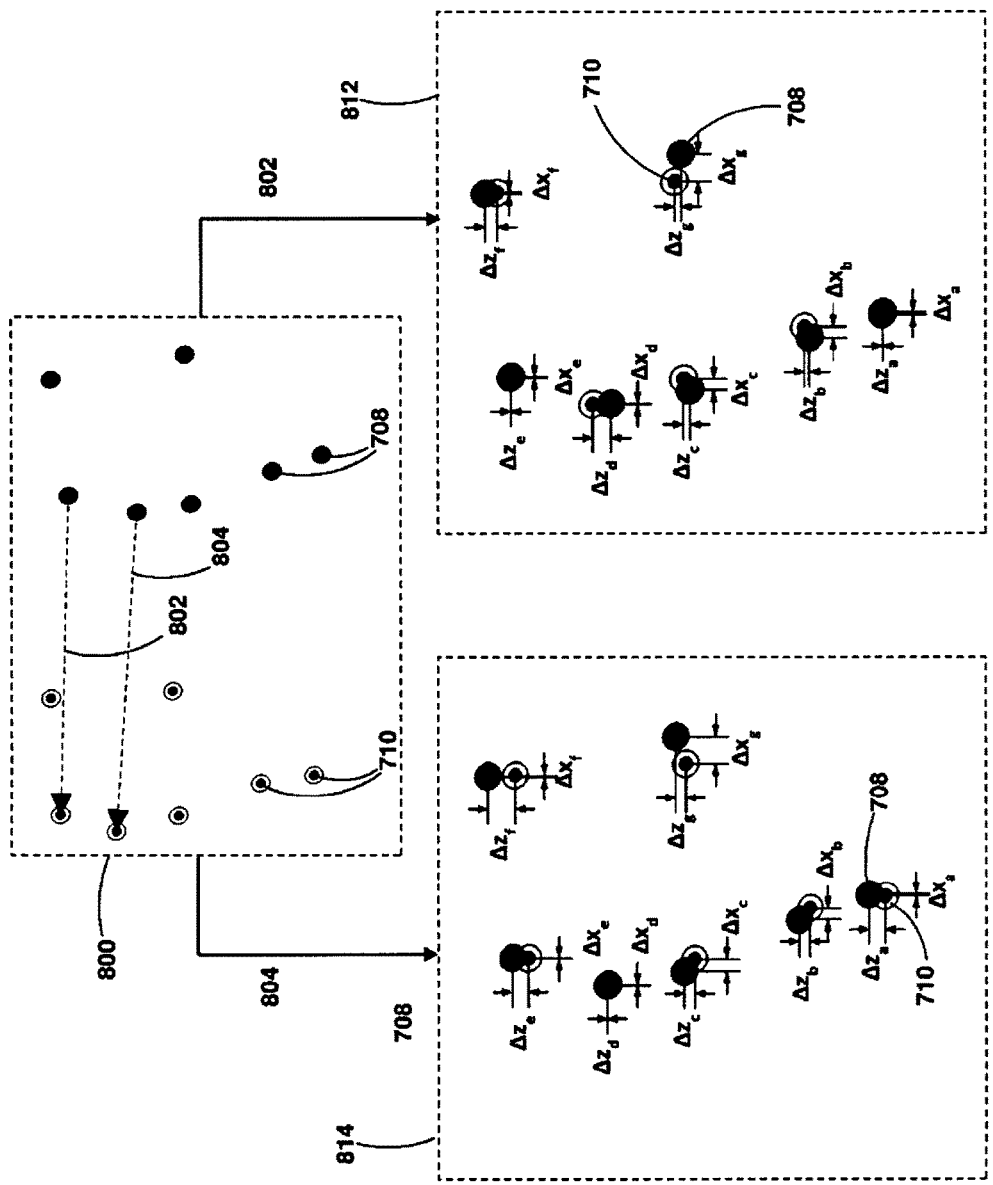
FIG. 8 is a diagram depicting a transform by method 621 in FIG. 6.

Once the scanned fiducial points are extracted from the patient image 630, the following step 635 is to compute a patient registration transform. FIG. 7 depicts an illustration of a computed transform 712 as per the example provided. It is apparent from the figure that the transform 712 is computed such that the fiducial points 708 acquired from the physical coordinate space align with the extracted fiducials 710. In general the completion of this step 635 requires the navigation system processor to compute a single transform that when applied to each fiducial point 708 in the image space individually, will align them with their scanned fiducial counterparts 710. However given practical limitations of technology perfect alignment is problematic to achieve for all of the fiducial points using a single transform. Thus to approximate a perfect alignment the processor instead computes a transform that minimizes the deviation in alignment between the extracted fiducials from the patient image and the fiducial points on the patient. For example as shown in FIG. 8 the transforms 802 and 804 both attempt to align the fiducial points 708 with their counterparts 710 in the image space 800. Such transforms may be derived by iteratively applying a cost minimization function to the initial set of fiducial points with arguments being the sum of spatial deviances $\Delta x_{a \to g}$ and $\Delta z_{a \to g}$ between the two sets of points 708 and 710 For example as shown in FIG. 8 the iterative computation may in one iteration produce the transform 804 that when applied to the fiducial points 708 produces the alignment of points shown in frame 814 of FIG. 8. While in a subsequent iteration may produce the transform 802 that when applied to the fiducial points 708 produces the alignment of points shown in frame 812 of FIG. 8. The processor may then execute the cost minimization function to compare the sum of the deviances $\Delta x_{a \to g}$ and $\Delta z_{a \to g}$ for each result 814 and 812 and select the one with the lowest value for the next iteration and so on until the deviation value falls below a certain threshold value or meets some alternately defined criteria. It is apparent from the case shown in FIG. 8 that the transform which minimizes the spatial deviances $\Delta x_{a \to g}$ and $\Delta z_{a \to g}$ when applied to the fiducial points 708 is the transform 812. It should be noted that in the example provided in the figure the deviances are shown in two dimensions however this should not be taken to limit the number of dimensions over which these iterative cost minimization functions may be applied.

Referring back to FIG. 6, once step 635 is completed and a patient transform is derived it may then be used to transform any points from the physical coordinate space of the operating room into the image space, effectively coupling the two spaces. Referring back to FIG. 7 this aspect of the patient registration process is illustrated by the physical coordinate space 720 and the image space 735 where the spatial alignments between the patient 707, the patient reference 760, and the pointer tool 702 is duplicated by the virtual representations of these objects in the image space 735. i.e. by the patient scan 706, the virtual patient reference 762 and the virtual pointer tool 714 in the image space 735.

Figure 6:
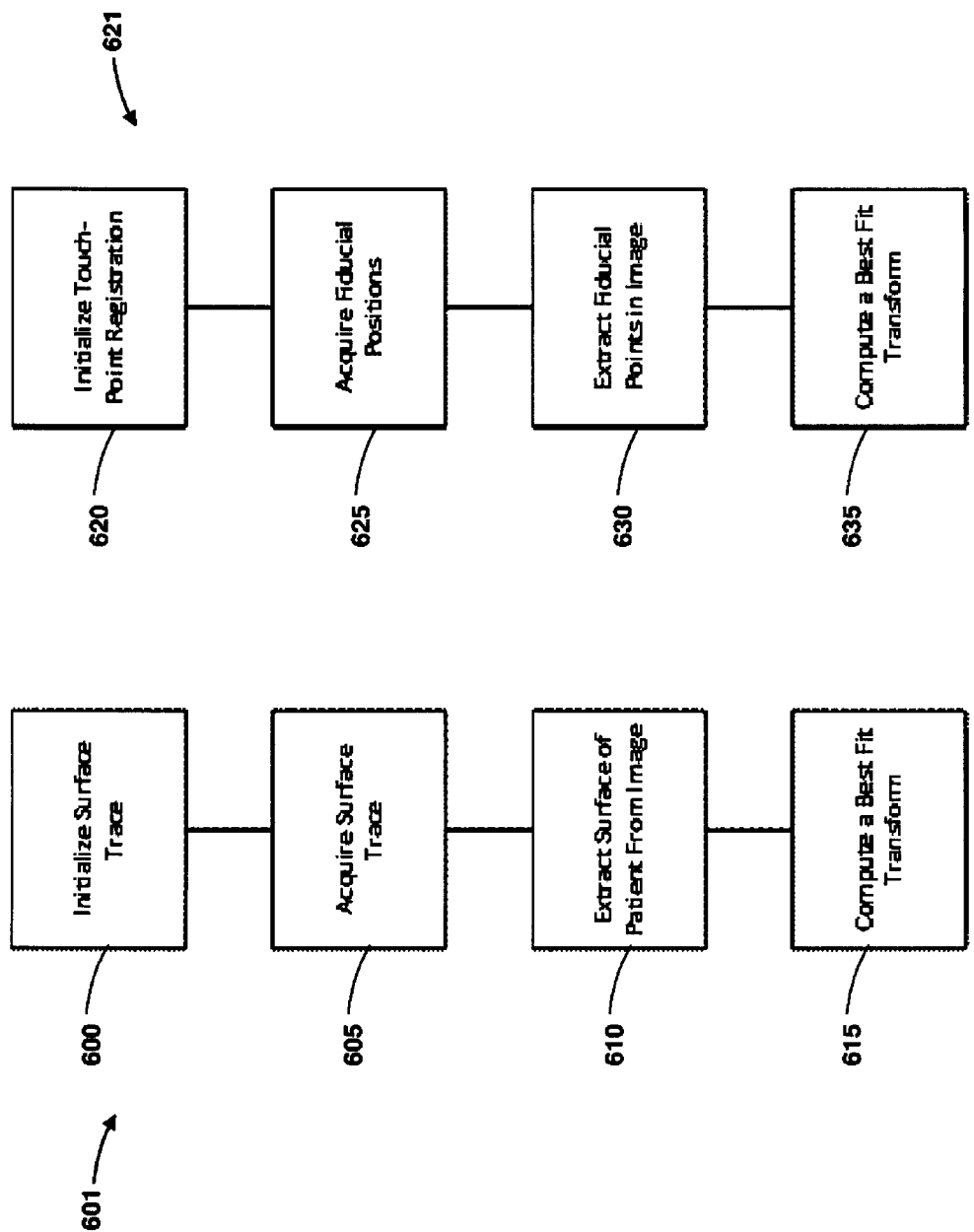
FIG. 6 is a flow chart illustrating two methods of registering a patient for a medical procedure with a medical navigation system.
Figure 9:
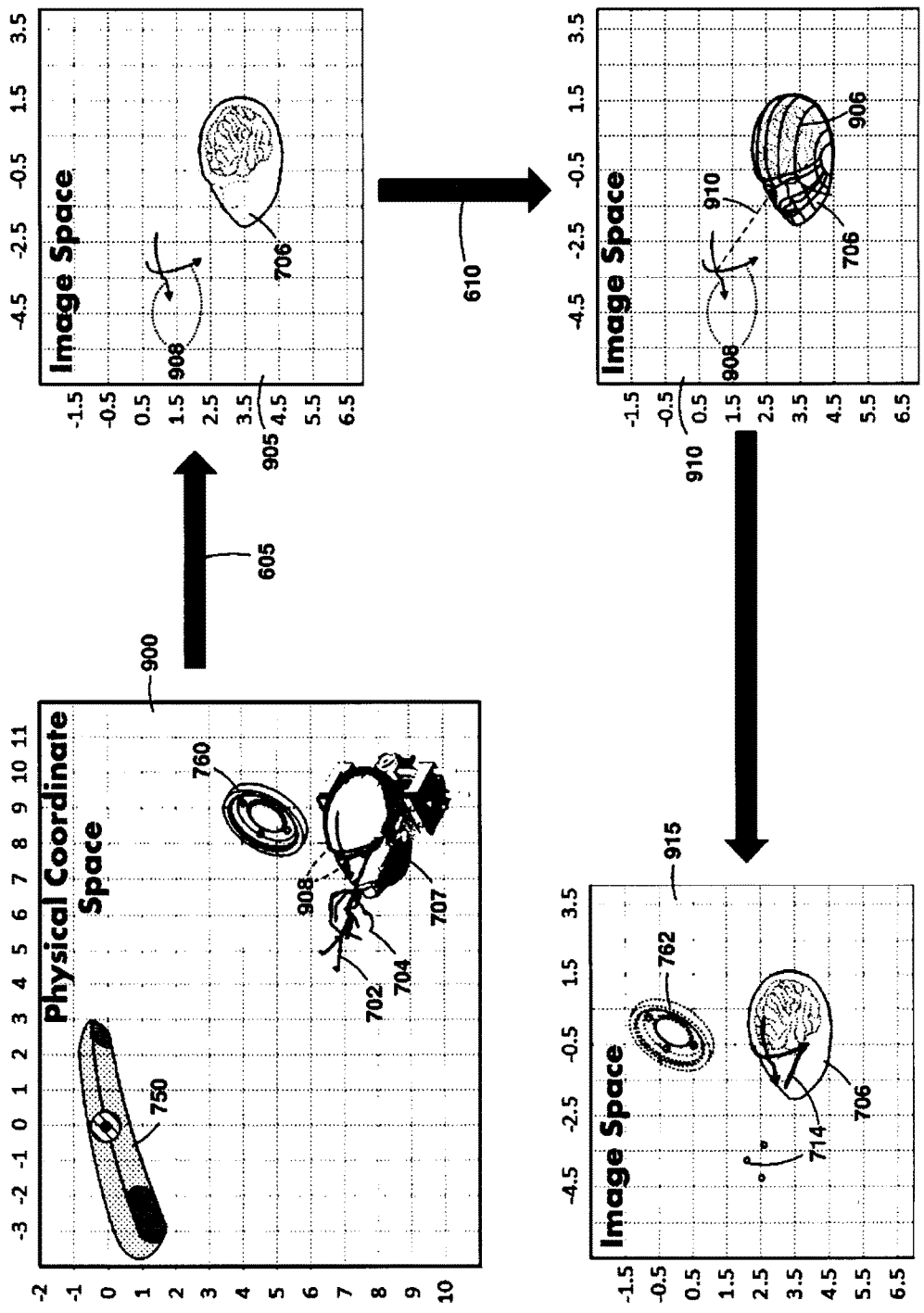
FIG. 9 is a diagram depicting method 601 of the methods in FIG. 6.

Returning to the flow charts in FIG. 6, the second flow chart 601 describes the process of a surface trace patient registration. FIG. 9 shows an illustrative diagram of each step in performing a patient registration using the surface trace method 601. This method may be implemented using a surgical navigation system as is known in the art and any steps may be programmed into the processor and stored in memory and recalled as needed.

The first step in this method 600 is to initialize the surface trace patient registration process. During this step a user may prompt the navigation system processor such as processor 302 in FIG. 3 to prime itself to receive one or more surface traces of the patient. To clarify a surface trace generally refers to a set of point positions acquired sequentially, that are identified by guiding a tracked tool over the contours of a patients surface features by the tracking system. However, it should be noted that alternatively to point positions any data type able to represent the contours of the patient may be used instead, such as vectors, curves and the like. In some instances as opposed to the user initializing the surface trace patient registration process an alternate embodiment would be the system itself may initiate a surface trace registration process without the input of the user, such as upon the system advancing to the patient registration step, or upon detection of trackable medical instruments in the operating room (for example, via tracking system 321), or upon other indicative actions. One such action could be detected by the navigation system, such as for example the navigation system determining that the pointer tool tip has dwelled at the same position for a predetermined period of time. To elaborate further, a user may allow the pointer to dwell in a position until the navigation system processor recognizes this action and begins serially acquiring positions of the pointer at which time the surgical navigation system may notify the user that it has begun capturing positions for the surface trace by producing an audible signal, or in an alternate embodiment may notify the user through the display and GUI of the navigation system. In some instances the surgical navigation system may indicate to the user that a trace has begun or ended using an audible signal such as a click or a continuous tone until the trace ends. The termination of a trace (i.e. the point at which the navigation system stops serially acquiring positions of the pointer tool) may in some instances be prompted by many of the trace inducers described above. Furthermore, in addition to dwelling, another gesture that may be used to terminate the trace would be a fast movement of the pointer. This embodiment could be implemented by comparing each new position of the pointer in the series with the previous position of the pointer and checking to see if that value falls within some tolerance value. In yet another embodiment the trace may terminate if the pointer tool position becomes undetectable. For, example if the pointer tool leaves the field of view of the camera.

Once the surface trace registration process is initiated 600 the following step 605 is to acquire one or more surface traces in the physical coordinate space of the operating room. FIG. 9 depicts an illustration of this step 605. As is shown in the figure a user 704 is guiding a tracked pointer tool 702 along the contours of a patient's face 707 to acquire the two surface traces 908. The tracking camera 750, connected to the surgical navigation system, collects the positions of the surface trace points 908 via the tracked pointer tool 702 and passes them to the navigation system processor which stores the points in the image space containing the patient image, such as the points 908 in the image space 905, in the processor memory, or alternatively any known coordinate space. In some instances the tracking system may be continuously tracks the pointer tool's position in order to record the positions of the pointer tool during the surface trace (i.e. when it is guided across the features of the patient). During this instance the system may be prompted by the user to begin or end the trace. This prompt may be facilitated through the use of a switch type device such as a foot pedal or mouse that are connected to the surgical navigation system or in alternate embodiments may be determined by the inertial state of the pointer tool as determined by the tracking system component of the surgical navigation system. It should be noted that further ways of beginning or ending the trace are described above in more detail.

Once the surface traces are acquired 605 the following step 610 is to extract the surface from the patient image. FIG. 9 depicts an illustration of this step 610. As is shown in the figure the image of the surface 906 of the patient is extracted from the patient image 706 in the image space 910. In some cases the extraction of the surface from the image of the patient may be completed by the combination of a user and a processor through a GUI. While in other cases the surgical navigation system may be programmed with instructions to extract the surface of the patient from the patient image from automatically. In yet alternate cases the surface may be provided in a useable form (i.e. to compute a surface trace patient registration via surface matching) by the 3D imager which acquired the image. Thus step 610 may be performed by either a user or an automated system such as a surgical navigation system processor.

Once the surface of the patient is extracted from the patient image 610 the following step is to compute a patient registration transform 635. FIG. 9 depicts an illustration of a computed transform 910 as per the example provided. It is apparent from the figure that the transform 910 is computed such that the surface traces 908 acquired from the physical coordinate space align with the extracted surface contours 906 (and also consequently the patient image). In general the completion of this step 635 requires the navigation system processor to compute a single transform that when applied to each surface trace 908 in the image space individually, will align them with the extracted surface 906 of the patient image 706. However given practical limitations of technology perfect alignment is problematic to achieve for all of the points (or equivalents) in one or more surface traces using a single transform. Thus to approximate a perfect alignment the processor may instead derive a transform that minimizes the deviation in alignment between the surface 906 extracted from the patient image 706 and the surface traces 908 acquired from the patient. However, given the practical limitations of perfect alignments other algorithmic variants may be used alternatively to the minimization described above. For example, weighting certain traces and areas of the extracted surface for greater importance may be used to provide better overall results. To elaborate further upon weighting the traces the cost minimization function may not depend on a purely one to one alignment error. For example, if weighting is added to some traces or some single points or some areas on the surface of the patient, then the application of a computed transform may result in some regions being better aligned to the traces than the rest.

Figure 10:
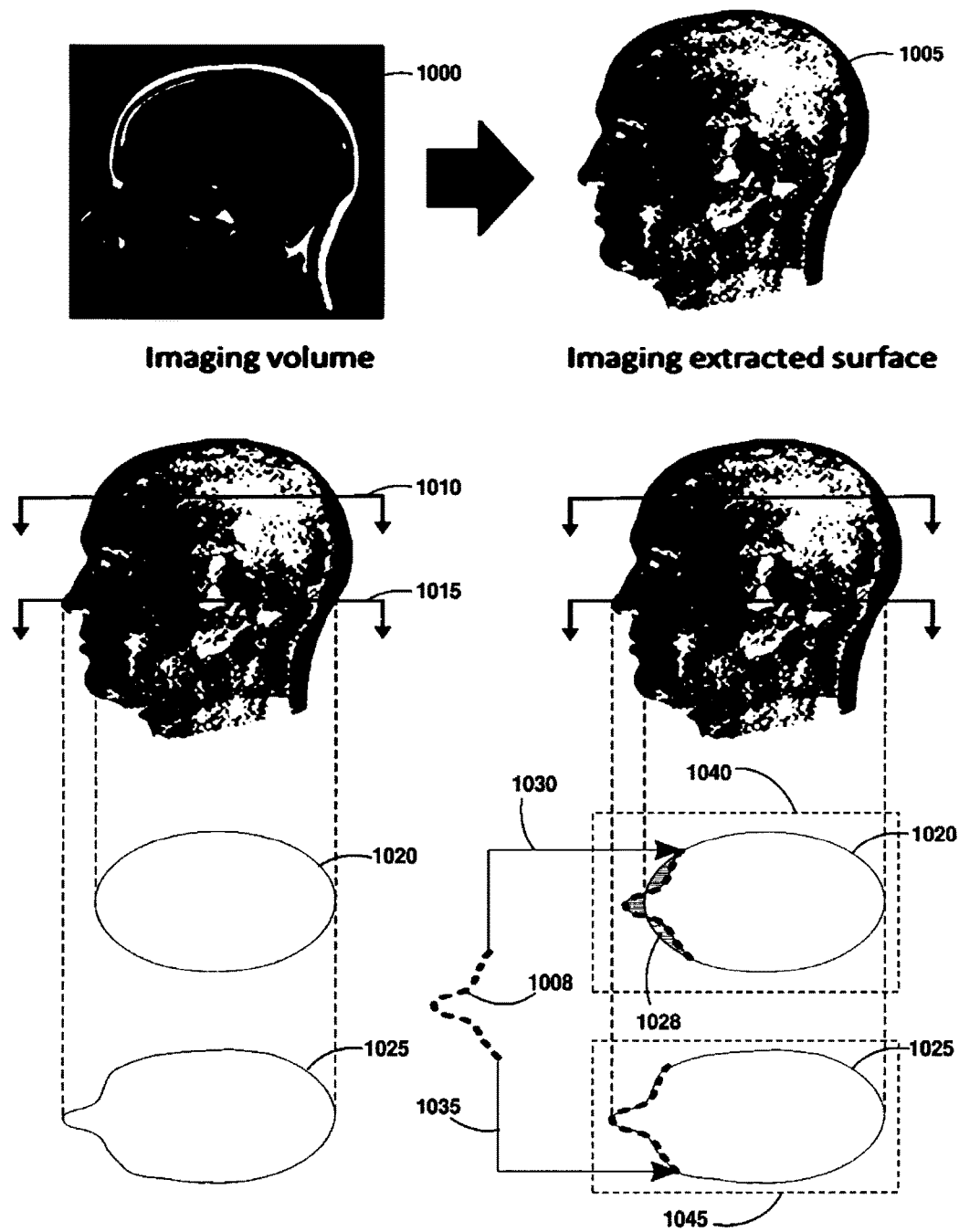
FIG. 10 is a diagram depicting a transform by method 601 in FIG. 6.

For example FIG. 10 shows an exemplary diagram depicting the computation of a transform from a surface trace 1008 to an extracted surface contour. As is apparent from the figure a patient image 1000 is processed to extract its surface 1005. Two contours 1020 and 1025 of the extracted surface 1005 are also provided for illustrative purposes. The figure also contains a single surface trace 1008 acquired from the patient that was scanned such as the patient 707 shown in the previous figure. Two transformations 1030 and 1035 are shown and applied to the surface trace 1008. Such transforms may be computed by iteratively applying a cost minimization function to the initial surface trace with arguments being the sum of spatial deviance 1028 between the surface traces 1008 and the extracted surface of the patient 1005. In one example, the iterative cost minimization function may take the form of an Iterative Closest Point (ICP) approach to calculate the registration transformation, such as that detailed in "A Method for Registration of 3-D Shapes" by Paul J. Besl and Neil D. McKay, IEEE Transactions on Pattern Analysis and Machine Intelligence, pp. 239-256, VOL. 14, No. 2, February 1992, the entirety of which is hereby incorporated by reference. However, any suitable approach may be used depending on the design criteria of a particular application. Continuing with the description of computing the transform via minimizing the spatial deviances 1028 as shown in FIG. 10 the iterative computation may in one iteration produce the transform 1030 that when applied to the surface trace 1008 produces the alignment shown in frame 1040 of FIG. 10. While in a subsequent iteration may produce the transform 1035 that when applied to the surface trace 1008 produces the alignment shown in frame 1045 of FIG. 10. The processor may then execute the cost minimization function to compare the sum of the deviances for each result 1030 and 1035 and select the one with the lowest value for the next iteration and so on, until the deviation value falls below a certain threshold value or meets some alternately defined criteria. It should be noted that the term spatial deviances as used herein may refer to Euclidean distances between the two sets of points for which the deviance is being calculated.

Referring back to FIG. 6, once step 635 is completed and a transform 910 is derived it may then be used to transform any points from the physical coordinate space of the operating room into the image space; effectively coupling the two spaces. Referring back to FIG. 9 this aspect of the patient registration process is illustrated by the physical coordinate space 900 and the image space 915 where the spatial alignments between the patient 707, the patient reference 760, and the pointer tool 702 is duplicated by the virtual representations of these objects in the image space 915. i.e. by the patient scan 706, the virtual patient reference 762 and the virtual pointer tool 714. It should be noted that even though the surface contours 906 were extracted in the image space, in some instances they may be removed or made invisible if desired. This may help reduce visible occlusions of the patient image when a surgeon is operating by using the GUI of the navigation system.

Figure 11:
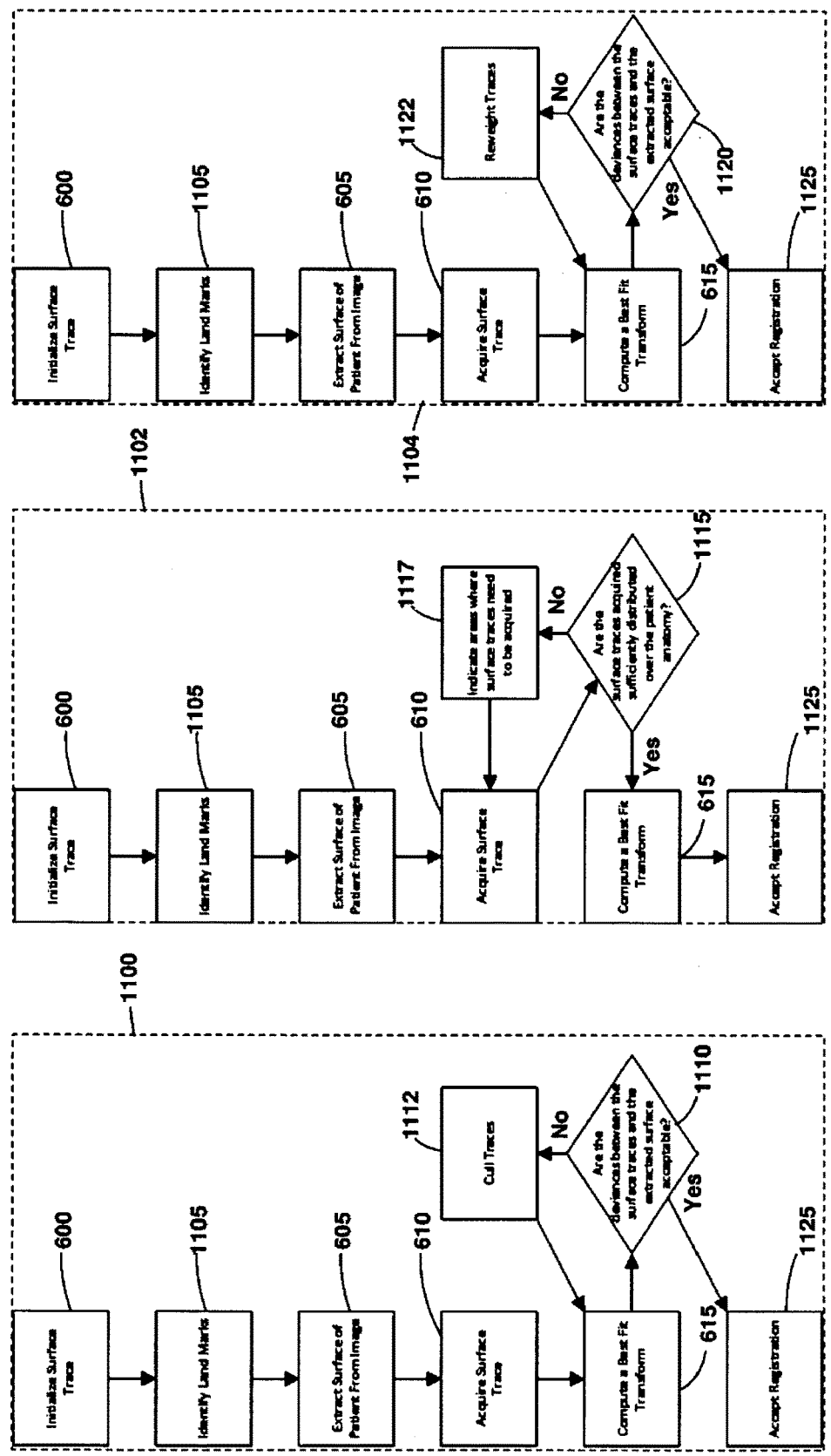
FIG. 11 illustrates three flow charts describing further enhancements to method 601 in FIG. 6.

One aspect of the present application provides for methods to improve the effectiveness of the computed patient transform for a surface trace patient registration process. Whereby applying the methods may provide better alignment between points on the patient in the physical coordinate space and the extracted surface of the patient image. In some instances the first of these methods allows the user to modify the acquired surface traces post-acquisition in an attempt to remove any outliers or points that cause the alignment to worsen. In some instances the second method involves the use of the processor, and through a counting procedure, informs the user of an unbalance in the spatial distribution of points across the different regions of the patient's anatomy. In some instances the third method involves the aspect of weighting the traces so deviances between some surface traces and the extracted surface of the patient may minimized. In some instances the fourth method involves the use of combining registration methodologies to produce a better result. Accordingly FIG. 11 provides flow charts describing the first three methods. These flow charts describe the methods as an augmentation of the surface trace patient registration method outlined in FIG. 6. More specifically these methods incorporate new steps in the surface trace patient registration that may improve the outcome of the registration.

It should be noted that the additional step 1105 of identifying landmarks shown in each of the methods 1100, 1102, and 1104 streamlines the computation of the transform in the surface trace patient registration process by providing an initial estimate of the patient transform. This is accomplished by identifying at least three points on the patient and deriving a transform similar to the touch point method described above. Once completed the outputted registration transform from this step may be used as an initial estimate in the first iteration of a computation used to derive a final patient registration transform such as previously described. For example, the transform outputted by step 1105 may be used as an initial estimate in the iterative surface trace method described in FIG. 6 or it may be incorporated with alternate methods such as those shown in FIG. 11. It should be noted that since this process is only used to compute an initial estimate of the patient registration transform, unlike the touch point method above, the identification of landmark positions (such as the nasion, temple, and tip of the nose, among others) need not necessarily be so exact. i.e. the identification of landmarks may not require the use of fiducials. In addition the corresponding positions of the landmarks on the patient image may be manually identified by the user or automatically determined by the processor.

Figure 12:
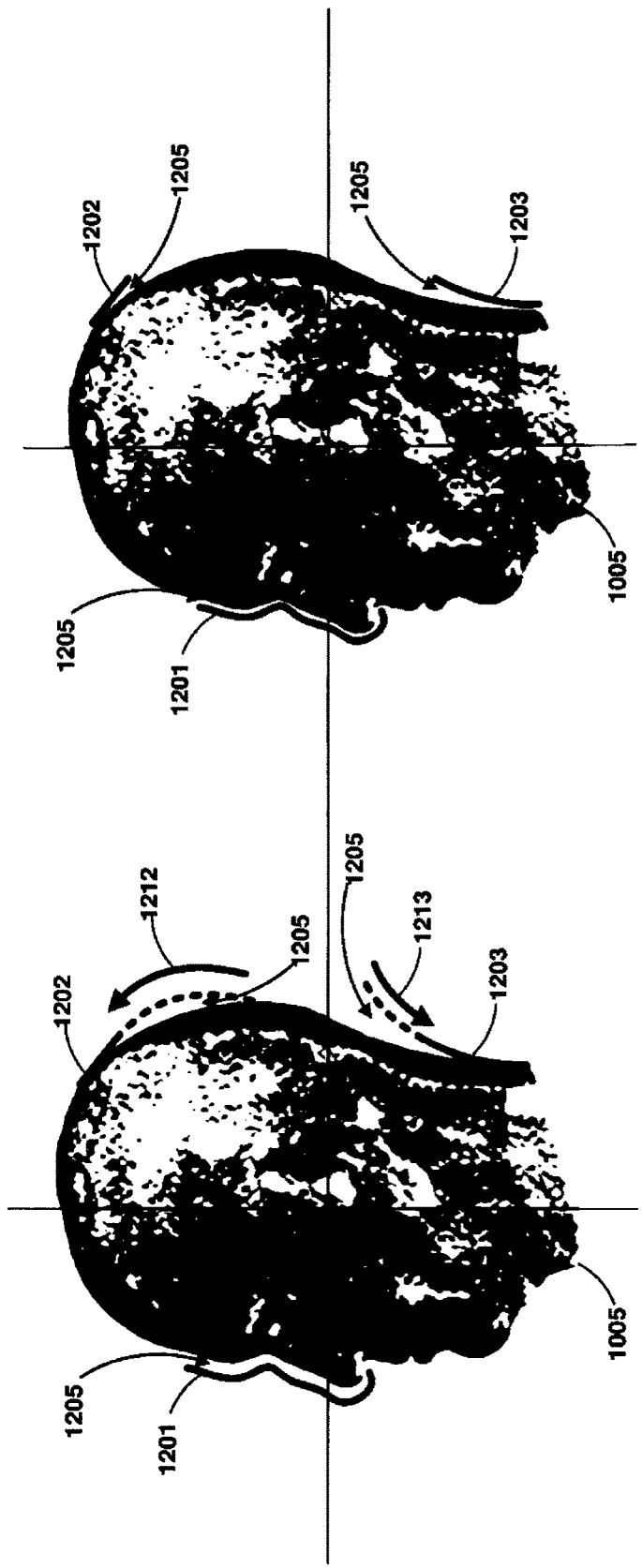
FIG. 12 is a diagram depicting the effect of the first enhancement in FIG. 11.
Figure 13:
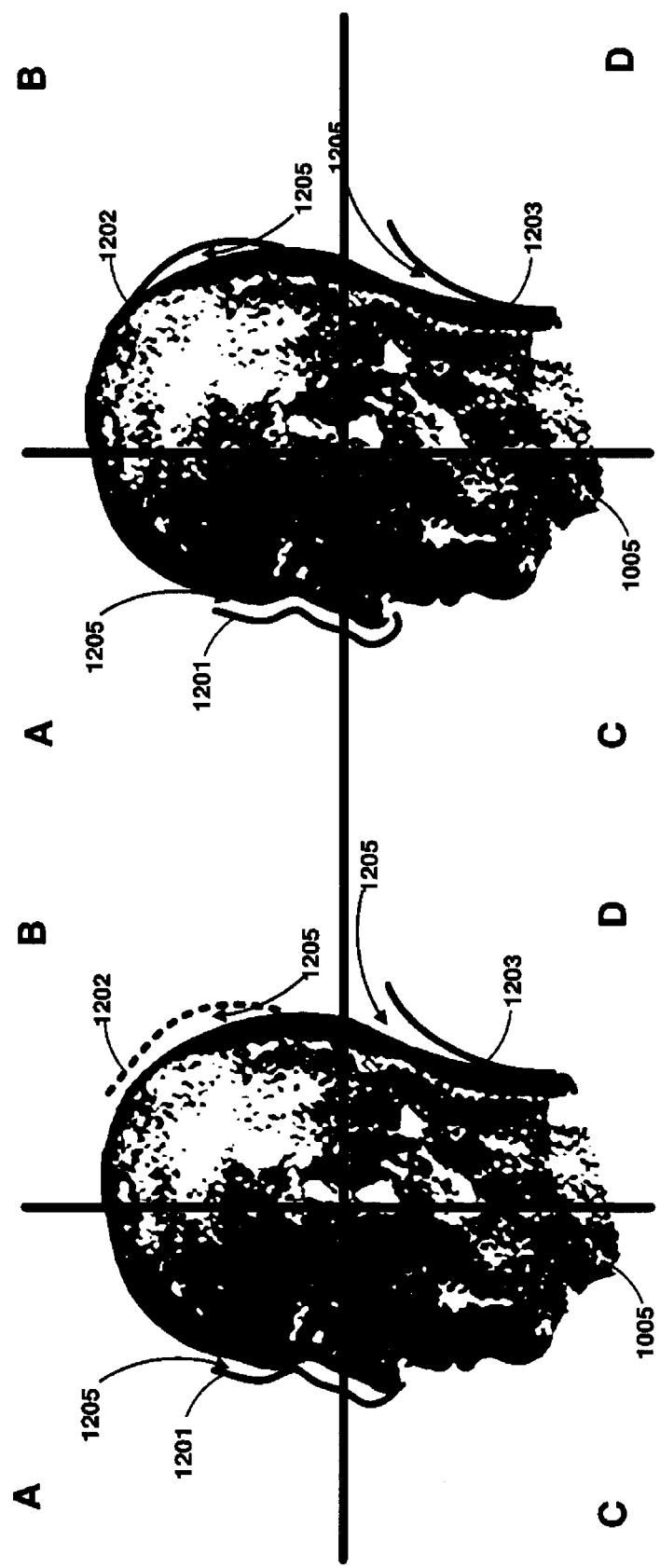
FIG. 13 is a diagram depicting the effect of the second enhancement in FIG. 11.

Returning to the flow charts in FIG. 11 the first flow chart 1100 describes how the computed transform used for patient registration may be improved via the culling of surface traces acquired in step 610 of the surface trace registration process. The additional loop of culling the traces follows the computation step 615 and involves the decision step 1110 and the action step 1112. The decision step 1110 requires the user or in alternate embodiments the processor to determine whether the sum of deviations of the one or more surface traces from the extracted surface of the patient image is under a threshold value which is acceptable. If the deviations are acceptable then the patient registration is completed using the computed transform 1125. If the deviations are not acceptable then the surface traces are culled at step 1112, a new transform is computed at step 615 and the loop repeats until a transform which produces an acceptable amount of deviances is found. An example implementation of the culling step 1112 is provided in FIG. 12. The left side of the figure shows an extracted surface from a patient image 1005 overlaid with transformed surface traces 1201, 1202, and 1203 before any of the traces have been culled. As is apparent from the figure there is a significant amount of deviation between the extracted surface 1005 and the surface traces at areas 1205. This deviation may be caused by many factors such as human error for example the pointer tool tip being removed from the surface of the patient at the end of a surface trace, or practical limitations to do with the image space having a limited resolution, or the accuracy of the tracking system in converting coordinates from the physical coordinate space to the image space, or any other sources of error that may have affected the patient registration. Nonetheless one way to account for some of this error, such as the accidental lifting of the tool from the patient, would be to cull the trace over that region. For example given the tail end (dashed segment) of surface trace 1203 was acquired when the pointer tool was removed from the surface of the patient then culling the surface trace at that region, for example as indicated by arrow 1213, may reduce the minimum deviation of the optimal transform computable by the processor of the navigation system. In addition in areas of the head having hair (not visible on patient image) a surface trace may have many regions of inaccurate points because of the hair occluding the surfaces needed to acquire and accurate trace. For example, given such was the case for the tail end of surface trace 1202 then removing (culling) this area as indicated by arrow 1212 may also reduce the minimum deviation of the optimal transform computable by the processor of the navigation system. Referring back to FIG. 12 the right side of the figure shows the results of the fit of the surface traces after the culling of the two traces 1212, and 1213 were applied. It is apparent that after the culling the fit of the surface traces is better and more specifically the deviations in areas 1205 of the right side of the figure are reduced Returning to the flow charts in FIG. 11 the second flow chart 1102 describes how the computed transform used for patient registration may be improved via increasing the spatial coverage of the surface traces acquired in step 610 of the surface trace registration process. The additional loop of assuring sufficient spatial coverage of the surface traces follows the surface trace acquisition step 610 and involves the decision step 1115 and the action step 1117. The decision step 1115 requires the user or in alternate embodiments the processor to determine whether the spatial distribution of points derived from the surface traces are sufficiently distributed over the patient anatomy. If the deviations are acceptable then the patient registration is completed using the computed transform 1125. If the deviations are not acceptable then the processor indicates areas on the patient image 1117 where further surface traces are needed. The process then returns to the acquire surface trace stage 610 and the loop is repeated until the system captures enough surface traces to assure sufficient coverage of the patient image. FIG. 13 illustrates the concept of distribution of the surface traces over the patient anatomy. The left side of the figure shows an extracted surface from a patient image 1005 overlaid with transformed surface traces 1201, 1202, and 1203 before trace 1202 has been acquired by the processor (hence why it's dashed). As is apparent from the figure there is a significant amount of deviation between the extracted surface 1005 and the surface traces at areas 1205. This deviation may be caused by many factors such as described above. However it is also apparent from the figure that the fit of the acquired surface traces to the data is more vertically deviated than horizontally deviated. This is more apparent when observing the nose alignment with the trace 1201. One reason this deviation may have occurred would be as a result of not sufficiently acquiring points from all of the regions of the head of the patient. For example the acquisition of points tend to be mid to bottom heavy and balanced between the left and right. Thus the fit of the trace tends toward the upper areas of the scan. As indicated above, one way to address this shortcoming is to identify to the user that they have not acquired points that are sufficiently distributed on the patient's anatomy and prompt them for more distributed traces. For example, given the processor may segment the patient image in FIG. 13 into regions A, B, C, and D. Then from the left side of FIG. 13 it is apparent that the surface traces 1201 and 1203 cover quadrant regions A, D, and C, of the patient image but not quadrant B, thus in step 1117 the system may indicate to the user that they should acquire a surface trace in that region (i.e. area B). After subsequently acquiring a surface trace, such as trace 1202, and recalculating the patient registration transform it is apparent from the right side of FIG. 13 that the alignment of the patient image with the surface traces is now more vertically balanced. Moreover the identification of regions of the patient where more traces should be acquired via step 1117 may be determined using additional metrics other than just the spatial distribution mentioned above. For example, traces acquired from regions of the patient having more pronounced features are generally more useful in computing a transform compared to their more uniform counterparts, as they tend to have less redundant geometries than other parts of the patient surfaces. To illustrate this concept when acquiring a surface trace of a patient head, the face in comparison to the left side of the head tends to have more unique geometries than the right side of the head in comparison to the left side of the head or the top in comparison to the back of the head. Thus when determining which regions require more coverage to prompt the user for acquisition, the navigation system processor may suggest areas based on the amount of unique features as opposed to simply the distribution of surface traces on the image. It follows then that in some instances the anatomical areas of the patient image may be used to define the regions that are used to determine the spatial distribution of traces over the patient.

Returning to the flow charts in FIG. 11 the third flow chart 1104 describes how the computed transform used for patient registration may be improved via the weighting of surface traces acquired in step 610 of the surface trace registration process. It should be noted that the term weighting as mentioned above refers to prorating the values of a particular surface trace when being used to compute the transform and in some instances this may involve normalizing a set of constants reflective of the relative ranking of each of the traces relative to one another. The additional loop of weighting the surface traces follows the computation step 615 and is comprised of the decision step 1120 and the action step 1122. The decision step 1120 requires the user or in alternate embodiments the processor to determine whether the sum of deviations of the one or more surface traces from the extracted surface of the patient image is under a threshold value which is acceptable. If the deviations are acceptable then the patient registration is completed and the transform 1125 computed. If the deviations are not acceptable then the surface traces are reweighted at step 1122, a new transform is computed at step 615 and the loop repeats until a transform which produces an acceptable amount of deviances is found.

Figure 14:
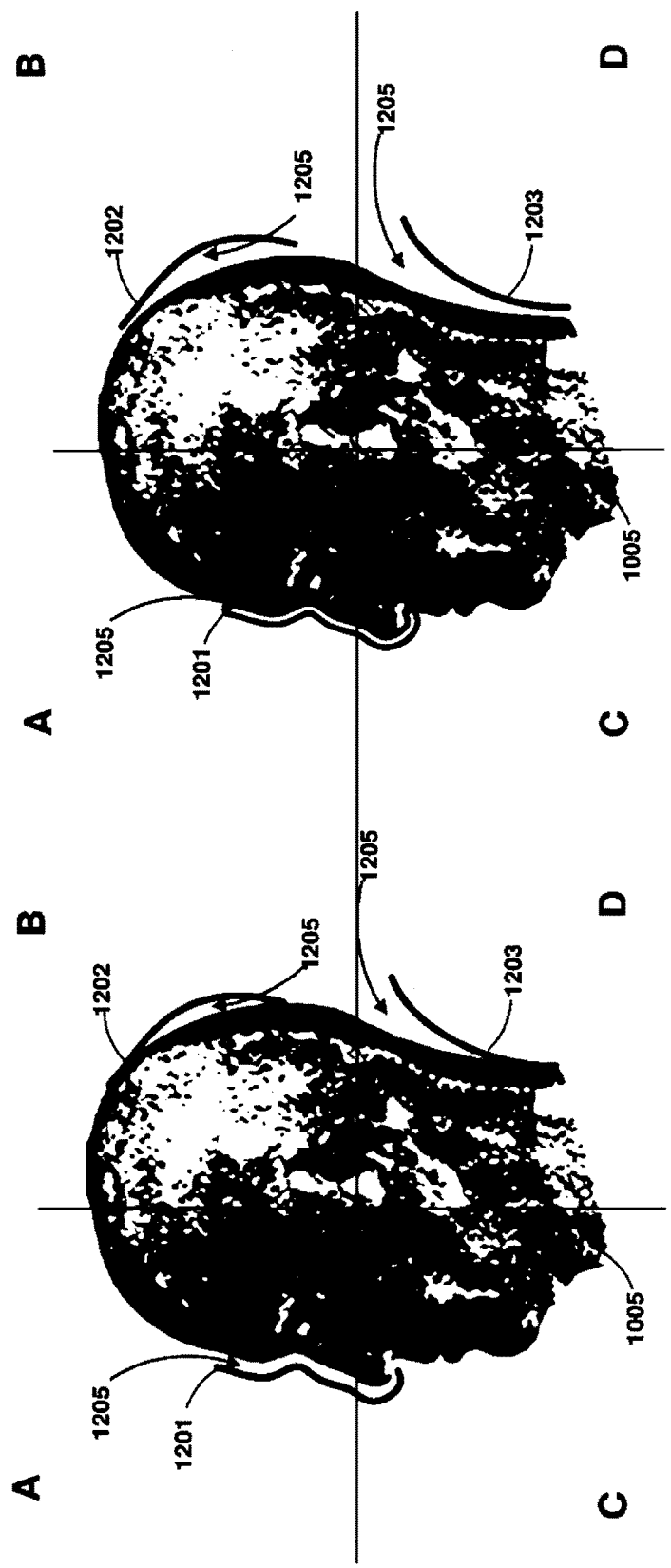
FIG. 14 is a diagram depicting the effect of the third enhancement in FIG. 11.

FIG. 14 illustrates the effects of applying a greater weight to a surface trace on the computed transform. The left side of the figure shows an extracted surface from a patient image 1005 overlaid with transformed surface traces 1201, 1202, and 1203 before any of the traces are ranked and weighted. As is apparent from the figure there is a significant amount of deviation between the extracted surface 1005 and the surface traces at areas 1205. This deviation may be caused by many factors such as outlined above. Nonetheless one way to account for some of these errors, such as the accidental lifting of the tool from the patient would be to reweight the trace in that region based on a ranking indicative of the traces accuracy or other factors. For example, given the surface trace 1201 was acquired without any preventable issues, while the acquisition of the other two surface traces did not proceed as smoothly it would make sense to rank the trace 1201 higher than the other two such that the deviance of each of the points from the surface trace 1201 would be weighted so each would have a greater value than its non-ranked version. For example, given the tail-end of the surface trace 1203 was acquired when the pointer tool was removed accidentally from the surface of the patient by the user, the surface trace 1202 was acquired by tracing the pointer tool over the occluding hair of the patient, and consequently the weighted surface trace 1201 was ranked double the other two traces, than each unit of distance that 1201 deviates from the extracted surface 1005 would be worth double of each unit of distance than either of the other two surface traces deviate from the extracted surface 1005. Thus referring back to the right side of FIG. 14 we can see that the weighted surface trace 1201 (shown as a double line because of the weighting) has more of an impact on the transform as per its greater influence because of its greater weight. It is apparent from the figure that the surface trace 1201 also resultantly influences the patient registration transform by orienting the extracted surface further into the left quadrants A and C as compared to their counterpart traces on the left side of FIG. 14 with no weighting.

In alternate implementations of the system and methods described herein the weighting factors as described above may be applied to individual segments that make up a trace as opposed to the trace itself. For example if a surface trace is made up of a plurality of points than the system as described herein may allow the user to weigh individual points or groups of points at different ranks, potentially magnifying the capacity of the user to attain the best patient registration. In another implementation the user may select points or groups of points via the same process in which a trace may be culled as described above. In some embodiments a slider may be used to indicate the segments of a surface trace (points, vector, amongst other constituent structures) to be culled or reweighted and a GUI may enable a user to indicate a weighting for those sections. In other embodiments the slider may be replaced by a switch in the form of a knob similar to a dimmer switch, or a text box allowing for an input such that the user may input an index referring to the sections to be reweighted or culled and their weights, the GUI may also allow the user to visually select or outline segments of the trace to be reweighted or culled using for example a cursor controlled by a mouse, and any other embodiments such that the user is able to identify the segment of the surface trace to be culled or reweighted. It should be noted that in this implementation, choosing a segment of a surface trace and subsequently assigning it a weight of 0 would affect the registration transform in effectively the same way as culling the same segment in the method described above.

In an additional implementation of the system and methods described herein the surface traces may be weighted based on an estimation of the quality of its acquisition. For example, referring again to FIG. 12 and process 1104 the step of reweighting the trace 1122 in the context of trace 1203 need not be applied broadly to the entire trace 1203 but instead could be segmented such that only the deviating portion of the tail-end 1213 would receive a lower weight, while the non-highlighted segment would retain its original weight.

In yet another implementation the unique weighting of the traces (or constituent structures) may be based on their effectiveness in computing the registration based on computational metrics. For example traces that are acquired from regions of the patient having more pronounced features are more useful in computing a transform compared to their more uniform counterparts as they tend to have less redundant geometries than other parts of the patient surfaces. To illustrate this concept when acquiring a surface trace of a patient head, the face in comparison to the left side of the head tends to have more unique geometries than the right side in comparison to the left side of the head or the top and the back of the head. Having an area with these less redundant features thus has a lower probability of an inaccurate registration. Moreover another metric that may be considered would be the density of points per volume of traces. For example a trace that has a 100 points covering an area of 5 $mm^2$ has many redundant points compared to a trace with 50 points covering an area of 5 $cm^2$. Thus weighting the second trace higher than the first will likely lead to the computation of a more accurate transform. It should be noted that the examples of weighting traces and their constituent structures as described above were to exemplify the system and methods as described herein and should not be construed to limit the invention and related concepts as disclosed.

Figure 15:
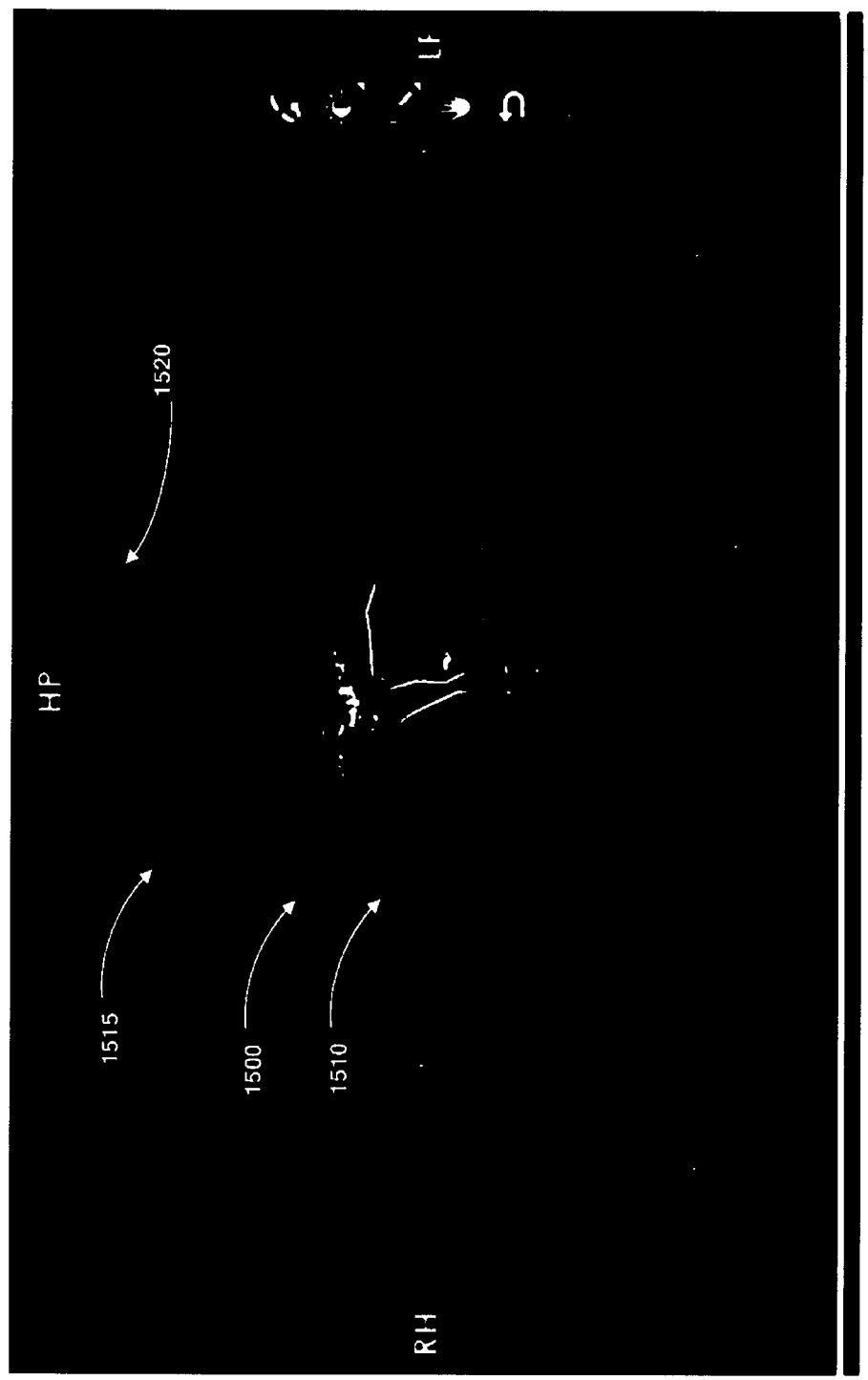
FIG. 15 is a diagram depicting a display showing a number of surface traces acquired after an initial alignment is provided for patient registration.

In some instances the methods mentioned above may be implemented by the surgical navigation system as shown in FIG. 3. More specifically any interaction between the user and the system may be performed through the use of the user interface 372 through a display such as that depicted in FIG. 2 and with medical instruments such as 360. More specifically any of the steps requiring analysis of the deviance of the surface traces and the extracted surface from the patient may be displayed to the user to provide information regarding the processes being executed such as for example, while acquiring surface traces after the initial estimate of the registration transform is calculated via step 1105 in FIG. 11. For example as shown in FIG. 15 a GUI showing two traces 1515 and 1510 visible atop an extracted patient surface 1500 may be used to determine whether the transform provides a sufficient accuracy or requires a refinement using one of the methods described herein. For example the gap between the surface trace 1515 and the extracted surface of the patient 1500 indicated by 1520 may provide the user with enough information to inform them that a refinement is needed. In addition in certain situations the trace may intersect the surface (not shown) which is also indicative of an inaccurate transform for the patient registration. Thus a user interface may be implemented to the benefit of the user in providing them real-time feed-back of the alignment of the surface traces with regards to the extracted surface of the patient during acquisition of the traces. This feature may help streamline the process of patient registration as opposed to completing the patient registration step and subsequently confirming the alignment, such as in the step 412 of FIG. 4, only to have to return to the previous step 406 of initiating the registration and completing the entire registration process again.

In some instances a method that may be used to improve the patient registration process involves using the touch-point registration as described above in combination with the surface trace registration as described herein. In this additional method, touch points may be added into the computation and may reduce the deviance between the surface trace points and the extracted surface of the patient image resulting in a better outcome. While in other embodiments such as during the computation of a patient-registration using the touch-point method described above an embodiment of which is shown as 621 in FIG. 6 the surface trace may be used to supplement missing touch-points or add more information that could be used to refine the patient registration and provide a better patient registration transform.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A method of performing a patient registration using a surgical navigation system, having a processor, in a medical procedure, comprising:
   initializing a surface trace acquisition;
   recording one or more surface traces;
   terminating the surface trace acquisition;
   receiving a patient image of a patient anatomy;
   extracting a surface from the patient image;
   computing a registration transform for patient registration between the one or more surface traces and the patient image extracted surface;
   segmenting the patient image into a plurality of regions, each region of the plurality of regions containing an anatomical landmark;
   determining a spatial distribution of surface traces among the plurality of regions;
   determining whether the spatial distribution in relation to each region of the plurality of regions minimizes deviance below a threshold; and
   if the spatial distribution in relation to any region of the plurality of regions is determined as exceeding the threshold, providing information relating to such region.

2. The method of claim 1, wherein computing a registration transform comprises minimizing a set of Euclidean distances.

3. The method of claim 1, wherein computing a registration transform comprises iteratively inputting registration transforms into a cost minimization function.

4. The method of claim 2, further comprising:
   initializing a fiducial position acquisition;
   recording the positions of fiducials on the patient; and
   receiving the location of fiducials points in the patient image.

5. The method of claim 1, further comprising the steps of:
   monitoring the position of a pointer tool;
   analyzing the position to determine if the pointer tool is motionless; and
   upon determining that the pointer tool is motionless for a predetermined amount of time, prompting the surgical navigation system to initialize or terminate the surface trace.

6. The method of claim 1, wherein computing a registration transform further comprises:

receiving input from a user ranking the one or more surface traces;
computing a weighting for the surface traces based on the ranking;
applying the weighting to the surface traces; and
computing a registration transform that minimizes a set of Euclidean distances between the one or more surface traces and the surface.

7. The method of claim 1, wherein computing a registration transform further comprises:
receiving input from a user of one or more regions of one or more surface traces to be culled;
discarding the one or more regions from the one or more surface traces; and
computing a registration transform that minimizes a set of Euclidean distances between the one or more surface traces and the surface after the regions have been discarded.

8. The method of claim 1, wherein computing a registration transform further comprises:
initializing one or more landmark acquisitions;
recording the positions of one or more landmarks on a patient;
receiving the position of one or more landmark points in the patient image; and
computing an initial registration transform that minimizes a set of Euclidean distances between the one or more landmarks and the one or more landmark points.

9. The method of claim 8, further comprising using the initial registration transform to visualize an initial alignment of the patient's position with the patient image in an image space.

10. The method of claim 9, further comprising visualizing the surface traces in the image space.

11. A surgical navigation system used for navigated surgical procedures, comprising:
a tracked pointer tool for identifying positions on the patient;
a tracking system for tracking the pointer tool;
a processor programmed with instruction to:
initialize a surface trace acquisition;
continuously record the positions of the pointer tool during the surface; trace acquisition;
combine the positions recorded during the surface trace acquisition into a surface trace;
terminate the surface trace acquisition;
receive a patient image of the patient;
extract a surface from the patient image;
compute a registration transform between the one or more surface traces and the surface for patient registration;
segment the patient image into a plurality of regions, each region of the plurality of regions containing an anatomical landmark;
determine a spatial distribution of surface traces among the plurality of regions;
determine whether the spatial distribution in relation to each region of the plurality of regions minimizes deviance below a threshold; and
if the spatial distribution in relation to any region of the plurality of regions is determined as exceeding the threshold, provide information relating to such region.

12. The system of claim 11, wherein the instruction to compute a registration transform comprises an instruction to minimize a set of Euclidean distances.

13. The system of claim 11 or 12, wherein the instruction to compute a registration transform comprises an instruction to iteratively input registration transforms into a cost minimization function.

14. The system of claim 12 or 13, wherein the processor is programmed with further instruction to:
initialize a fiducial position acquisition;
record the position of the pointer tool during the fiducial position acquisition; and
receive the location of fiducials points in the patient image.

15. The system of claim, wherein the processor is programmed with further instructions to:
monitor the position of the pointer tool with the tracking system by recording the pointer tool positions;
analyze the pointer tool positions to determine if the pointer tool is motionless; and
upon determining that the pointer tool is motionless for a predetermined amount of time, prompt the processor to initialize the surface trace acquisition.

16. The system of claim 11, wherein the instruction to compute a registration transform further comprises:
an instruction to receive input from a user ranking the one or more surface traces;
an instruction to compute a weighting for the surface traces based on the ranking;
an instruction to apply the weighting to the surface traces; and
an instruction to compute a registration transform that minimizes a set of Euclidean distances between the one or more surface traces and the surface.

17. The system of claim 11 or 16, wherein the instruction to compute a registration transform further comprises:
an instruction to receive input from a user of one or more regions of one or more surface traces to be culled;
an instruction to discard the one or more regions from the one or more surface traces; and
an instruction to compute a registration transform that minimizes a set of Euclidean distances between the one or more surface traces and the surface after the regions have been discarded.

18. The system of claim 16, further comprising a display having a GUI for receiving input from a user.

19. The system of claim 11, wherein the instruction to compute a registration transform further comprises:
an instruction to initialize one or more landmark acquisitions;
an instruction to record the positions of one or more landmarks on a patient;
an instruction to receive the position of one or more landmark points in the patient image; and
an instruction to compute an initial registration transform that minimizes a set of Euclidean distances between the one or more landmarks and the one or more landmark points.

20. The system of claim 19, further comprising a display and wherein the processor is programmed with further instructions touse the initial registration transform to visualize, on the display, an initial alignment of the patient's position with the patient image in an image space.

* * * * *